(12) United States Patent
Suslian et al.

(10) Patent No.: US 6,638,211 B2
(45) Date of Patent: Oct. 28, 2003

(54) METHOD FOR TREATING URINARY INCONTINENCE IN WOMEN AND IMPLANTABLE DEVICE INTENDED TO CORRECT URINARY INCONTINENCE

(75) Inventors: Patrice Suslian, Gordes (FR); Emmanuel Delorme, Chalon sur Saone (FR)

(73) Assignee: Mentor Corporation, Santa Barbara, CA (US)

(*) Notice: Subject to any disclaimer, the term of this patent is extended or adjusted under 35 U.S.C. 154(b) by 33 days.

(21) Appl. No.: 10/092,069

(22) Filed: Mar. 5, 2002

(65) Prior Publication Data
US 2002/0099260 A1 Jul. 25, 2002

Related U.S. Application Data

(63) Continuation of application No. PCT/FR01/02120, filed on Jul. 3, 2001, which is a continuation-in-part of application No. 09/661,620, filed on Sep. 14, 2000.

(30) Foreign Application Priority Data
Jul. 5, 2000 (FR) .............................. 00 08706

(51) Int. Cl.[7] ................................................ A61F 2/02
(52) U.S. Cl. ....................................................... 600/30
(58) Field of Search ............................... 600/29–32, 37; 606/141; 128/DIG. 25

(56) References Cited

U.S. PATENT DOCUMENTS

| | | | |
|---|---|---|---|
| 4,857,041 A | 8/1989 | Annis et al. | 600/30 |
| 5,013,292 A | 5/1991 | Lemay | 600/30 |
| 5,899,909 A | 5/1999 | Claren et al. | 606/119 |
| 5,934,283 A | 8/1999 | Willem et al. | 128/885 |
| 6,010,447 A | 1/2000 | Kardjian | 600/29 |
| 6,039,686 A | 3/2000 | Kovac | 600/30 |
| 6,042,534 A | 3/2000 | Gellman et al. | 600/30 |
| 6,042,536 A | 3/2000 | Tihon et al. | 600/37 |
| 6,074,341 A | 6/2000 | Anderson et al. | 600/29 |
| 6,110,101 A | 8/2000 | Tihon et al. | 600/37 |
| 6,117,067 A | 9/2000 | Gil-Vernet | 600/30 |
| 6,221,005 B1 | 4/2001 | Bruckner et al. | 600/30 |

FOREIGN PATENT DOCUMENTS

| | | | | |
|---|---|---|---|---|
| WO | WO 98/35606 | 8/1998 | | |
| WO | WO 98/35632 | 8/1998 | | A61F/2/02 |

*Primary Examiner*—Max F. Hindenburg
*Assistant Examiner*—Joseph A. Cadugan
(74) *Attorney, Agent, or Firm*—Fish & Richardson P.C., P.A.

(57) ABSTRACT

The invention relates to a method and device for treating urinary incontinence in women.

4 Claims, 2 Drawing Sheets

METHOD FOR TREATING URINARY INCONTINENCE IN WOMEN AND IMPLANTABLE DEVICE INTENDED TO CORRECT URINARY INCONTINENCE

CROSS REFERENCE TO RELATED FOREIGN APPLICATIONS

This application is a continuation of PCT application PCT/FR 01/02120 filed on Jul. 3, 2001 designating the United States, and published in French as WO 02/02031 on Jan. 10, 2002. PCT/FR 01/02120 claimed the priority of French Patent Application, serial number 00.08706, filed on Jul. 5, 2000. This application is also a continuation-in-part of U.S. Ser. No. 09/661,620, filed on Sep. 14, 2000. The entire disclosures of all are incorporated herein by reference.

The invention relates to a method for treating urinary incontinence in women. It also relates to an implantable device intended to correct urinary incontinence in women. The said device is more particularly suited to the treatment of stress urinary incontinence.

Various types of device have been proposed for treating phenomena of urinary incontinence in women.

Thus, for example, document U.S. Pat. No. 5,899,909 describes a tape of constant width, made of a material of the meshed or knitted polypropylene type ensuring fibroblast colonization and thus anchorage into the tissues along its entire length. Once an incision has been made in the wall of the vagina this tape is positioned under the urethra, the tape being led upwards on each side of the bladder to be anchored into the abdominal wall.

The method of fitting this tape is relatively tricky. Specifically, the needles being led vertically up alongside the bladder may not only pierce the latter, but may above all pierce the iliac artery or even the small intestine. In consequence, it is essential that cystoscopy be performed during the intervention.

Document WO 98/35632 describes a device in the form of a tape, the central region of which is wider than the body of the tape, the assembly being made of a biocompatible material, particularly a woven material, allowing for fibroblast colonization.

As before, each of the ends of the tape is led up alongside the bladder to be secured at the abdominal wall or, more specifically, in the bone of the pubis. Thus, the same drawbacks as before may be encountered.

One of the objects of the invention is to artificially reconstruct the pelvic fascia by fitting tapes aimed at restoring, as faithfully as possible, the effective and natural situation of the endo-pelvic fascia, in its role of fibrous plug obturating the urogenital opening, the said fascia resting on either side of the said opening on the floor of the lifting muscles.

Another of the stated objects of the present invention lies in solving the problems associated with subsequent surgical re-intervention in the region of the urethra; given the fact that the tapes proposed by the Prior Art are made, along their entire length, of a material capable of being colonized by fibroblasts, the problem arises of performing an intervention in this region if the tape, because of the fibroblast colonization, is anchored to the periurethral wall. A solution to this new problem is all the more important now that it has been found that the phenomenon of urinary incontinence may evolve to the fitting of an artificial sphincter. A problem such as this is neither disclosed nor suggested in the Prior Art.

Furthermore, the literature has described possible phenomena of the migration of the substance of which the tape is made, particularly polypropylene, into the viscera In order to solve all of these problems, the Applicant is proposing a method and an implantable device, intended to correct urinary incontinence in women.

This method for treating urinary incontinence in women comprises the following steps:
    making a mediane paraurethral incision, practically in the middle third of the urethra, measured from the meatus, so as to allow the passage of a tape between the Alban fascia and the periurethral fascias;
    extending each of the free ends of the said tape in the region of the two obturator foramen of the iliac wing and leading them out into the groin opposite the corresponding foramen so that they essentially form a V shape, the point of which V passes under the urethra without changing the position thereof.

In other words, and contrary to the surgical techniques employed in the state of the art, the tape is not led up alongside the bladder to form a U and thus be situated in close proximity to vital organs, but is on the contrary diverted from the bladder to form a V. Hence, no risk of damaging the bladder, the iliac artery or the small intestine is run. In consequence, it is not necessary to perform cystoscopy during the intervention.

According to the invention, in order to make it easier to fit the tape which acts as an implant, a space is made between, on the one hand, the Alban fascia, the perineal muscular plane and the anterior insertion of the puborectal muscle and, on the other hand, the periurethral fascias.

According to an advantageous version of the invention, the central region of the tape or implant, which region is intended to be inserted between the Alban fascia and the periurethral fascias, is coated with a substance capable of preventing any adhesion of the said fascias to the tape.

Thus it becomes possible to avoid any cell growth on the tape between the wall of the vagina and the wall of the urethra, hence avoiding any anchorage of the tape in this region and thus to allow subsequent surgical re-intervention. Furthermore, coating it with such a substance in the region of the urethra makes it possible to avoid any migration of polypropylene into the viscera.

The device according to the invention is characterized in that it is in the form of a tape of which the central region, intended to be inserted between the Alban fascia and the periurethral fascia, is coated with a substance capable of preventing any adhesion of the said fascias to the tape.

In a first embodiment, the substance that prevents adhesion of the fascias to the tape is silicone.

In a second embodiment, the substance is made of vegetable or animal growth factors.

Of course, any substance capable of avoiding the adhesion of the fascias to the tape may be envisaged.

The tape is coated on both side, advantageously on one side.

Furthermore, the tape is made of any materials such as those known to those skilled in the art and, in particular but without applying any limitation, any material chosen from the group containing polyethylene and polypropylene.

According to another feature, when the tape is made of polypropylene, the polypropylene is either meshed or knitted or alternatively is in the form of sprayed fibres. Nevertheless, the tape can also be made of absorbable material.

In one advantageous embodiment, the central region of the tape is not as wide as the rest of the tape and this is so as to limit the area of contact in the region of the Alban fascia and of the periurethral fascia.

Furthermore, and according to another feature, each of the ends of the tape has a tapered point intended to be anchored in the groin facing the corresponding obturator foramen.

According to a preferred embodiment, the tape has a length equal to 60 cm and a width equal to 2.5 cm, and has a central region which is not as wide, being 1 cm wide over a length equal to 3 cm. Advantageously, the central region has a length equal to 15 mm.

The invention and its ensuing advantages will emerge better from the following example in support of the appended figures.

Figure 1:
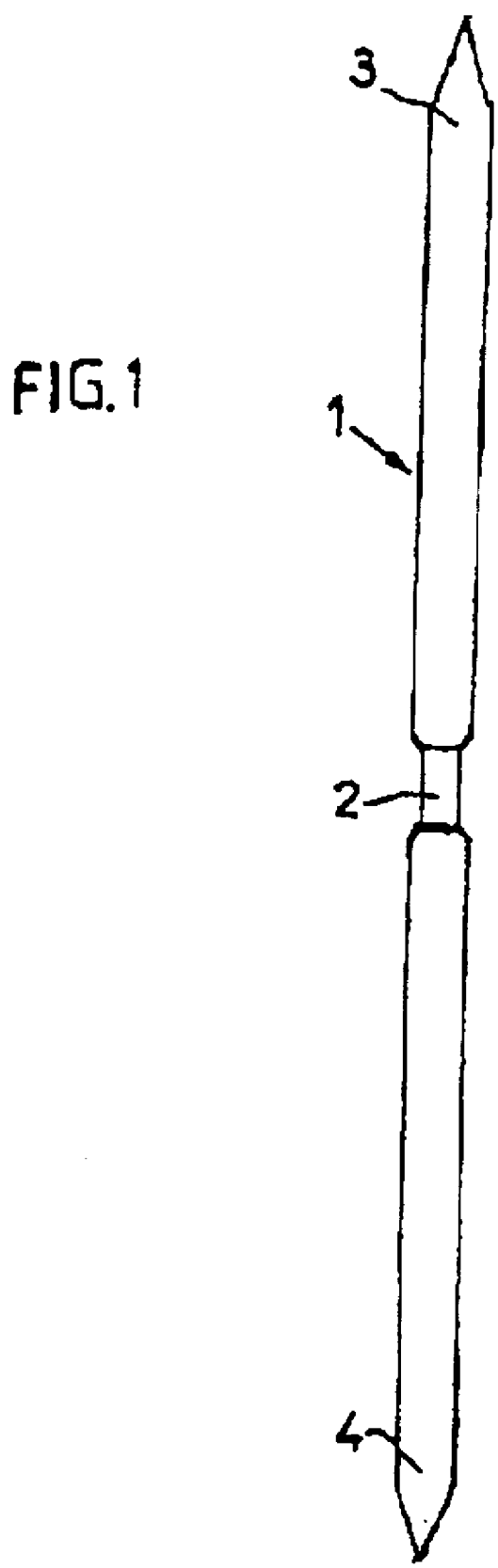
FIG. 1 is a diagrammatic depiction of the tape of the invention.

As shown in FIG. 1, the device of the invention is in the form of a tape (1) of a length equal to 60 cm and of a width equal to 2.5 cm. This tape is made, along its entire length, of sprayed polypropylene fibres.

According to an advantageous feature, the tape has, at its centre (2), a narrowing of length equal to 3 cm and of width equal to 1 cm, this portion being coated on both sides with a silicone-containing substance. Furthermore, each of its free ends (3, 4) is tapered.

Fitting the device requires mini-invasive surgery, the main steps of which are described hereinafter.

First of all, a mediane paraurethral incision is made in the region of the middle third of the urethra.

One of the two obturator foramen, and more specifically the lower internal part is then identified by a finger slipped into the vaginal incision and an incision is made in the perineal skin opposite it, and so in the groin, so as to form an orifice through which an Emmet needle is then passed. This needle is introduced through this cutaneous incision firstly perpendicular to the perineum for about 15 mm (passing through the internal obturator muscle as far as just outside the ischiopubic branch), then the needle is allowed to describe its curvature, guided in this by the finger introduced opposite the obturator muscle through the vaginal incision. The pointed end of the tape is then slipped into the eye of the needle, emerging from the said vaginal incision, then pulled back through the thickness of muscle, the retractor and the internal obturator up to the surface of the skin.

The tape is then placed between the Alban fascia and the periurethral fascias to position it in such a way that its central region, coated with silicone as appropriate, faces the said fascias. The tape is positioned without pulling behind the urethra.

An incision is then made in the perineal skin facing the second obturator foramen, into which incision an Emmet needle is inserted. The free end of the tape is then slipped into the eye of the needle which is pulled back in the same way as before.

The excess tape is then cut off flush with the skin then the skin is immobilized to disconnect it from the tape. The incision is finally closed with a stitch of quickly absorbable suture.

Figure 2:
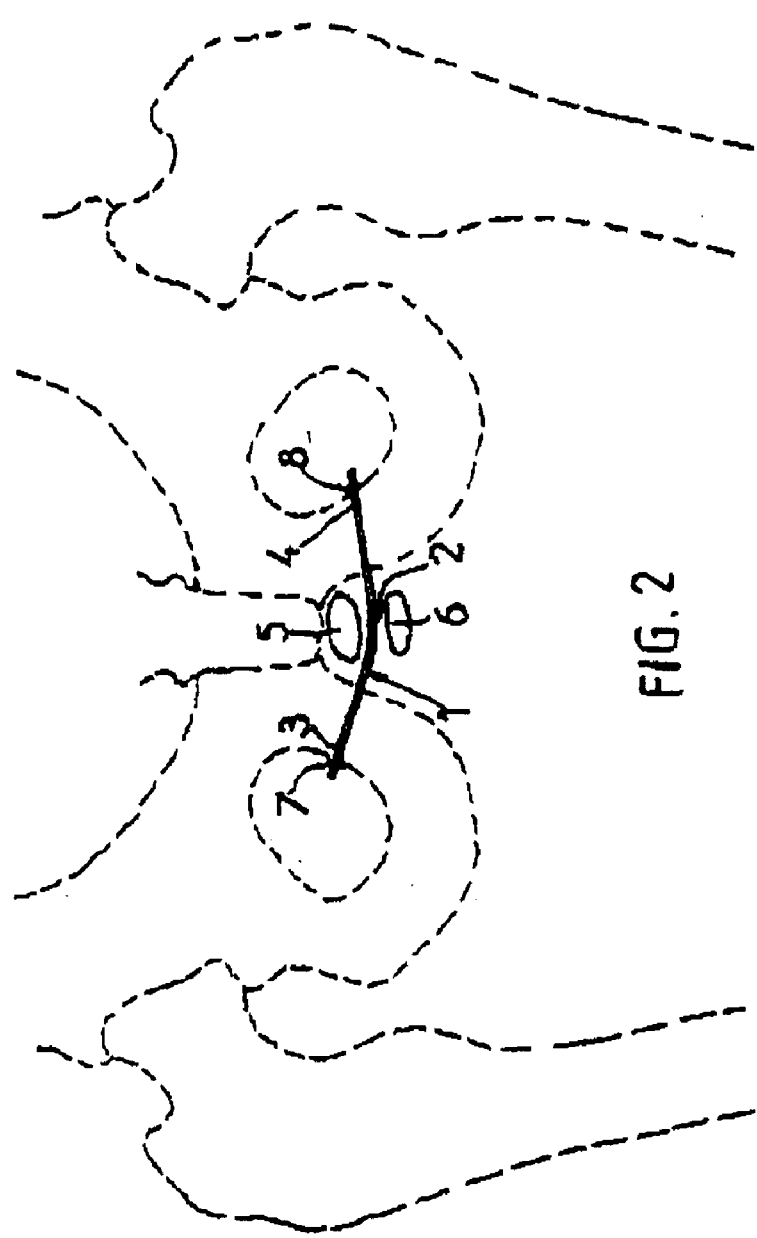
FIG. 2 is a diagrammatic depiction of the position of the tape after fitting.

FIG. 2 diagrammatically depicts the position, in cross section, of the tape after it has been fitted. As shown in this figure, once in place, the tape adopts the shape of a V, the branches of which are very far apart.

Furthermore, it can also be seen that when the tape according to one of the advantageous embodiments of the invention is used, the silicone-coated segment of the tape is positioned between the uterus (5) and the vagina (6), while its ends (3, 4) are secured in the region of the groin (7, 8) facing the obturator foramen.

Thanks to the robustness and texture of the tape, tension can be strong without there being any risk of rupture. The tape is positioned under the control of sight without employing cystoscopy. It is essential that there be no pulling on this tape which has to be slipped down under the urethra without altering the position thereof.

It is apparent from the foregoing that the method according to the invention for treating urinary incontinence in women differs from the methods proposed in the state of the art through the simplicity of fitting of the tape, using mini-invasive surgery. Furthermore, it provides the urethra with firm suspension while at the same time maintaining a certain degree of flexibility and, most of all, keeping the vital organs in the vicinity relatively far away from the said tape. Furthermore, it plays a part in reconstructing the endopelvic fascia.

What is claimed is:

1. Method for treating urinary incontinence in women, comprising:

making a median paraurethral incision, practically in the middle third of the urethra, measured from the meatus, so as to allow the passage of an implant in the form of a tape between the Alban fascia and the periurethral fascias; extending each of the free ends of said tape in the region of two obturator foramen of the iliac wing and leading them out into the groin opposite the corresponding foramen so that they essentially form a V shape, the point of which V passes under the urethra without changing the position thereof.

2. Method for treating urinary incontinence in women according to claim 1, characterized in that in order to make it easier to fit the tape which acts as an implant, a space is made between, on the one hand, the Alban fascia, the perineal muscular plane and the anterior insertion of the puborectal muscle and, on the other hand, the periurethral fascias.

3. Method for treating urinary incontinence in women according to claim 2, characterized in that the central region of the tape or implant, which region is intended to be inserted between the Alban fascia and the periurethral fascias, is coated with a substance capable of preventing any adhesion of the said fascias to the tape.

4. Method for treating urinary incontinence in women according to claim 1, characterized in that the central region of the tape or implant, which region is intended to be inserted between the Alban fascia and the periurethral fascias, is coated with a substance capable of preventing any adhesion of the said fascias to the tape.

* * * * *